US00PP28609P3

(12) United States Plant Patent
Suphachadiwong

(10) Patent No.: US PP28,609 P3
(45) Date of Patent: Nov. 7, 2017

(54) *VANDA* PLANT NAMED 'SPCDW1507'

(50) Latin Name: ***Vanda* Jones ex R. Br.**
Varietal Denomination: SPCDW1507

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 14 days.

(21) Appl. No.: 14/999,700

(22) Filed: Jun. 16, 2016

(65) Prior Publication Data

US 2016/0374249 P1 Dec. 22, 2016

(30) Foreign Application Priority Data

Jun. 19, 2015 (QZ) ..... PBR 2015/1387

(51) Int. Cl.
*A01H 5/02* (2006.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen Redden
(74) *Attorney, Agent, or Firm* — Samuel R. McCoy, Jr.

(57) ABSTRACT

A new and distinct *Vanda* cultivar named 'SPCDW1507' which is characterized by unique purple-violet sepals and petals which are heavily dotted and blotched with a dark violet color, ruffled sepal and petal margins, and the stability of these characteristics from generation to generation.

3 Drawing Sheets

Latin name of the genus and species: The Latin name of the genus and species of the novel variety disclosed herein is *Vanda* Jones ex R. Br.

Variety denomination: The inventive variety of *Vanda* disclosed herein has been given the variety denomination 'SPCDW1507'.

CROSS REFERENCE TO RELATED APPLICATIONS

This application claims priority to the Community Plant Variety Rights application number 2015/1387, filed Jun. 19, 2015, which is herein incorporated by reference.

BACKGROUND OF THE INVENTION

Parentage: The *Vanda* variety 'SPCDW1507' is the result of a planned breeding program. The new variety originated as a seedling from the crossing of an unnamed *Vanda* seed parent (not patented) with an unnamed *Vanda* pollen parent (not patented). Both parents were developed by, and are owned by, the inventor and were never commercially released. The crossing was made by the inventor in his research greenhouse in Bangphra, Thailand in May of 2003.

The new variety was first selected in February of 2008, in a research greenhouse in Bangphra, Thailand belonging to the inventor. After identifying the new variety as a potentially interesting selection, the inventor continued confidential testing and propagation of 'SPCDW1507', assessing stability of the unique characteristics of this variety.

Asexual Reproduction: Asexual reproduction of the new cultivar 'SPCDW1507', by way of mericloning, was first initiated in April of 2008 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1507' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1507'. These characteristics in combination distinguish 'SPCDW1507' as a new and distinct *Vanda* cultivar:

1. *Vanda* 'SPCDW1507' exhibits sepals and petals with a unique purple-violet color; and
2. *Vanda* 'SPCDW1507' exhibits sepals and petals which are heavily dotted and blotched dark violet; and
3. *Vanda* 'SPCDW1506' exhibits sepals and petals with ruffled margins.

BOTANICAL DESCRIPTION OF THE PLANT

Figure 1:
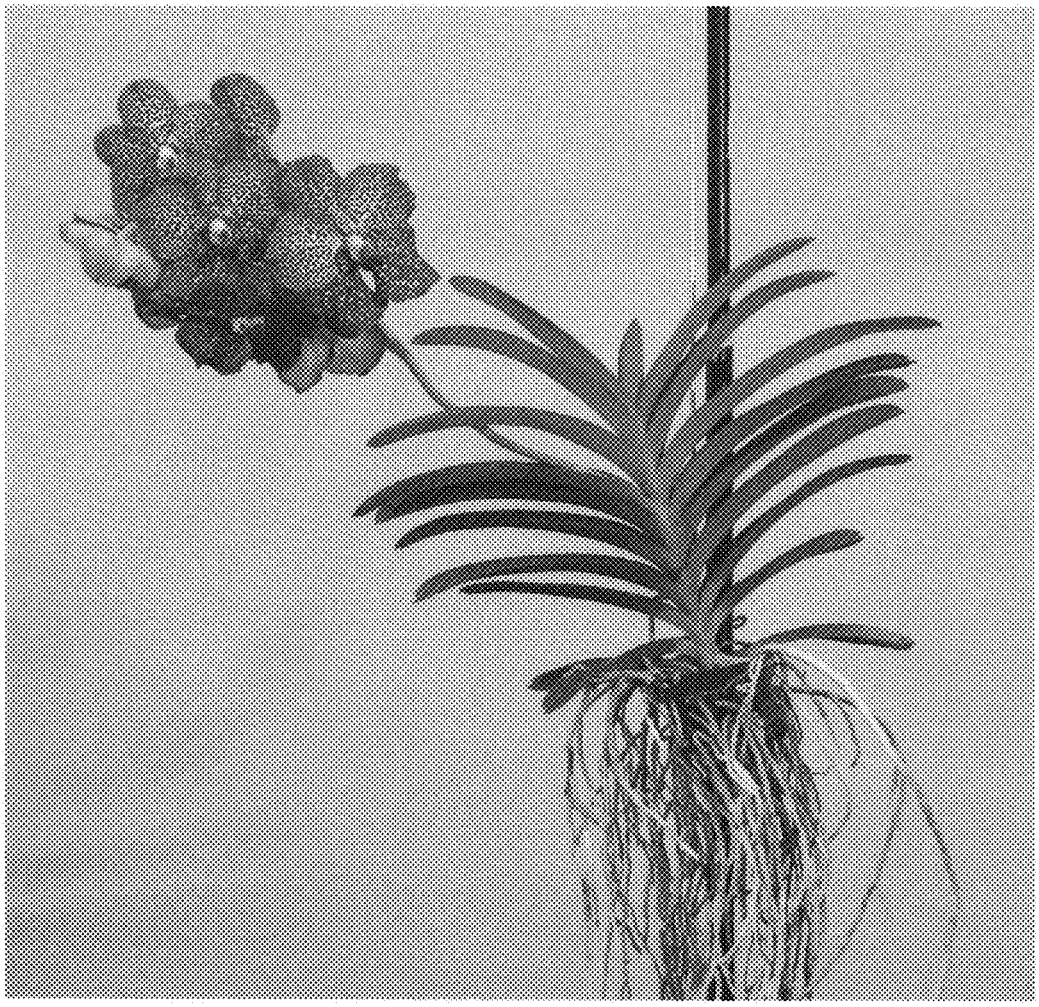
FIG. 1 illustrates, as nearly true as it is reasonably possible to make the same in color photographs of this type, an exemplary plant of 'SPCDW1507' grown in a commercial greenhouse in Honselersdijk, the Netherlands. This plant is approximately 6 years old from the time of mericloning, shown planted in an 8 by 8 cm container.
Figure 2:
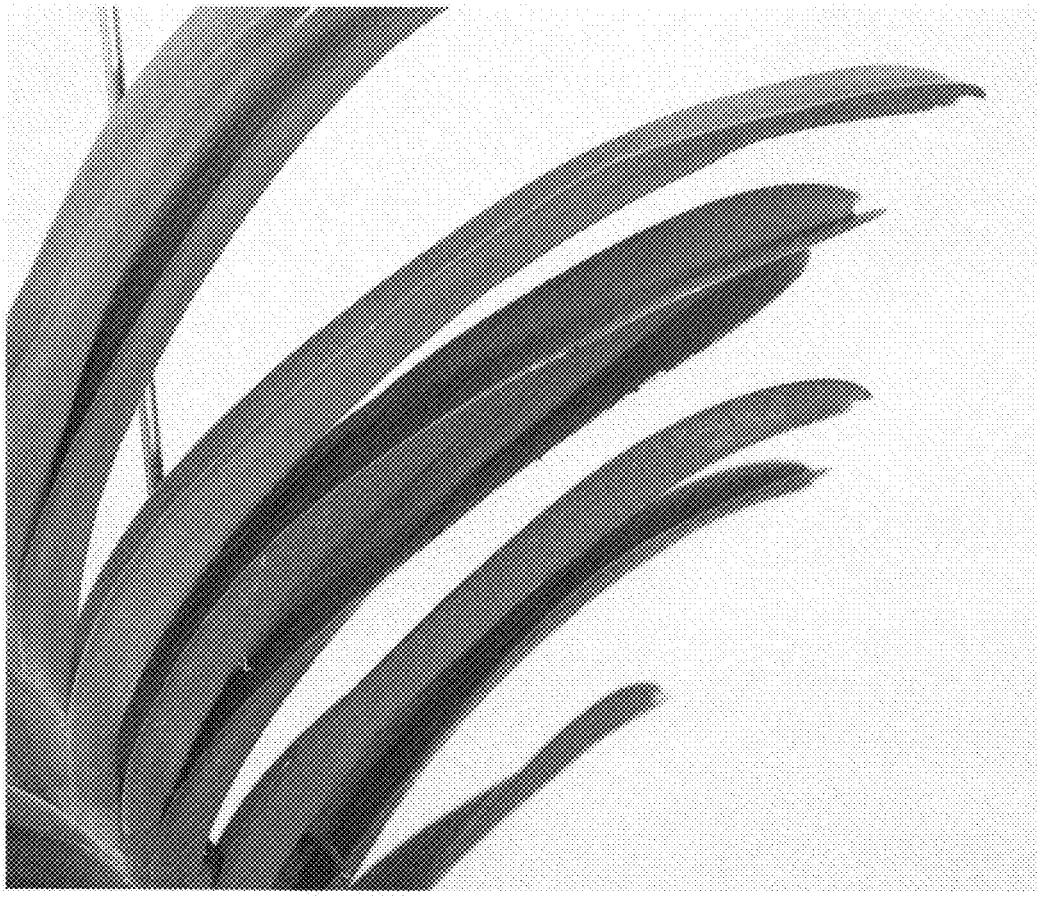
FIG. 2 illustrates, as nearly true as it is reasonably possible to make the same in color photographs of this type, the typical foliage of 'SPCDW1507'.
Figure 3:
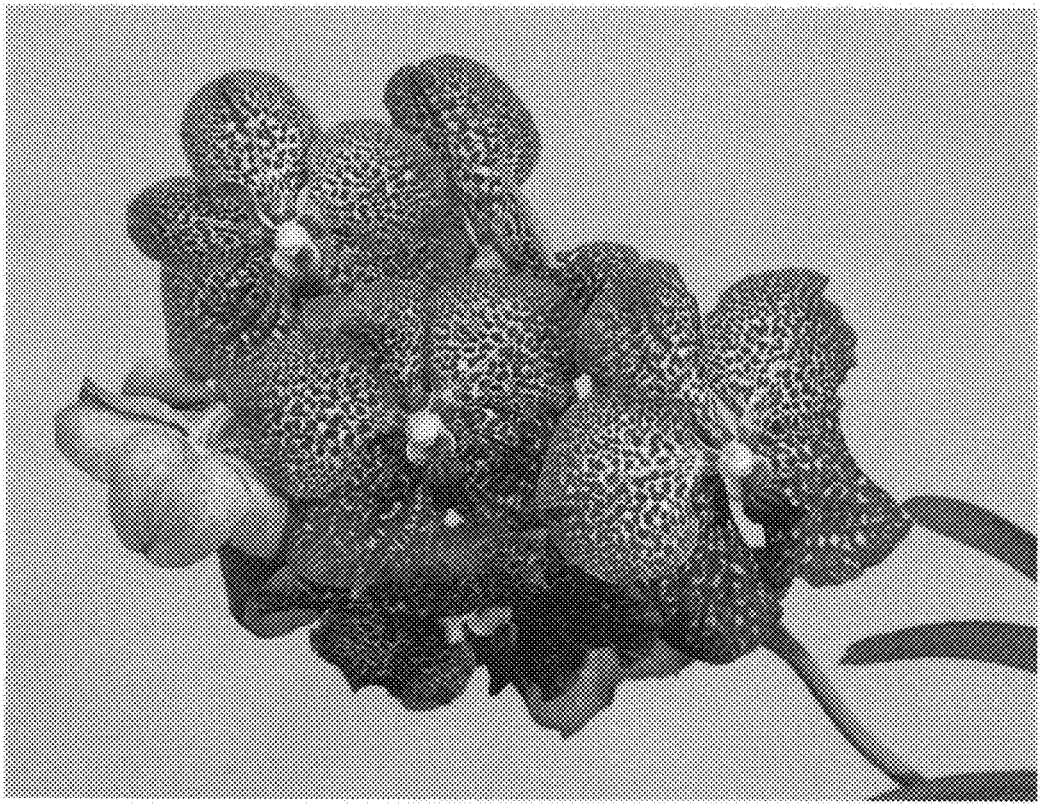
FIG. 3 illustrates, as nearly true as it is reasonably possible to make the same in color photographs of this type, the typical inflorescence and flower of 'SPCDW1507'.

The following observations and measurements made in April of 2016 describe averages from a sample set of six specimens of six year-old 'SPCDW1507' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1507' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1507' and comparisons with other varieties of *Vanda* are provided below.

Plant description:

- *Growth habit.*—Perennial; monopodial, upright. Single monopodial leafy stem, with flowers carried slightly above the leaf plane, inflorescences grow from the leaf axils.
- *Average height from base (plant grown in hanging basket, so no soil line present) to foliar plane.*—30.5 cm.
- *Average height from base (plant grown in hanging basket, so no soil line present) to top of floral plane.*—42.3 cm.
- *Plant spread.*—Average of 45.4 cm.
- *Appropriate container size.*—8 cm by 8 cm rectangular hanging basket.
- *Growth rate.*—Moderate.
- *Plant vigor.*—Moderate.
- *Propagation type.*—Tissue culture propagation using the base of the leaves.
- *Propagation details.*—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease and pest resistance or susceptibility.*—Similar to other *Vanda* varieties.
- *Environmental tolerances.*—Adapt to, at least, USDA Zones 11 and 12 and temperatures as high as 40 degrees Celsius; high tolerance to rain; moderate to high tolerance to wind.

Root system:

- *General.*—Densely rooting; with aerial roots only.
- *Dimensions, mature roots.*—57.2 cm long with a diameter of 0.5 cm, on average.
- *Texture.*—Very fleshy; non-fibrous.
- *Color.*—Greyed Green, near RHS 192B to 192C; root apex is yellow-green, RHS 147B to 147C.

Stem:

- *Branching habit.*—Monopodial; no lateral branches present.
- *Number of primary (main) stems per plant.*—One.
- *Number of secondary (lateral) branches per plant.*—None.
- *Appearance and shape.*—Circular, formed by the leaf sheaths.
- *Length.*—19.5 cm.
- *Diameter.*—0.9 cm.
- *Internode length.*—0.4 cm.
- *Luster.*—Matte.
- *Aspect.*—Near vertical.
- *Strength.*—Very strong.
- *Color, juvenile.*—Yellow-green, near RHS 150D.
- *Color, mature.*—Yellow-green, near RHS 150D.
- *Color at internodes.*—Yellow-green, near RHS150D.
- *Pubescence.*—Glabrous.

Foliage:

- *Arrangement.*—Distichous.
- *Quantity.*—Approximately 20 leaves per plant.
- *Dimensions.*—21.1 cm long and 3.0 cm wide, on average.
- *Shape of blade.*—Ligulate; moderately to strongly carinate.
- *Aspect.*—Slightly curved.
- *Apex.*—Unequal praemorse.
- *Base.*—Sheathing.
- *Sheath dimensions.*—3.2 cm long and 1.3 cm wide, on average.
- *Sheath color.*—Yellow-green, near RHS 150D.
- *Margin.*—Entire.
- *Pubescence, texture and luster of adaxial surface.*—Glabrous, smooth, and very slightly glossy.
- *Pubescence, texture and luster of abaxial surface.*—Glabrous, smooth, and matte.
- *Color.*—Juvenile foliage, adaxial surface — Yellow-green, near RHS 144A, and green towards the margins, near RHS 143A. Juvenile foliage, abaxial surface — Yellow-green, near RHS 144A. Mature foliage, adaxial surface — Green, near RHS NN137B. Mature foliage, abaxial surface — Yellow-green, in between RHS 144A and 146B.
- *Venation.*—Parallel.
- *Venation color, adaxial surface.*—Green, near RHS NN137B.
- *Venation color, abaxial surface.*—Yellow-green, near RHS 144B to 144C.
- *Petiole.*—No petioles present; leaves sessile.

Inflorescence:

- *Inflorescence arrangment.*—Axially placed raceme.
- *Natural flowering season.*—Autumn into winter.
- *Time to flower.*—Approximately 10 months.
- *Flowers per inflorescence.*—Average of 10; 9 open flowers and 1 buds.
- *Inflorescence height.*—Approximately 24.3 cm (measured from base of lowest flower to top of upper flower).
- *Inflorescence diameter.*—Approximately 17.9 cm.
- *Peduncle.*—Dimensions — Approximately 38.0 cm long and 0.7 cm wide. Aspect — Generally at a 30 degree angle to lateral branch axis; varying between 25 to 35 degrees. Strength — Moderately strong. Texture and luster — Glabrous and moderately glossy. Color — Yellow-green, RHS 145B.

Bud:

*Length.*—Average of 2.4 cm.

*Diameter.*—Average horizontal diameter is 2.3 cm; the vertical diameter is 2.5 cm.

*Shape.*—Cubic, with a deltoid apex which is pointed downward.

*Pubescence, texture and luster.*—Glabrous, smooth and matte.

*Color.*—Purple-violet, near RHS N82B; the apex is darker, near RHS N82A, and the base is purple, RHS 76C.

Flower:

*Flower type.*—Zygomorphic (orchidaceous), typical shape for the genus *Vanda*.

*Flowering habit.*—Moderate.

*Shape.*—Zygomorphic, single; consisting of three sepals and three petals, one of which is transformed into a labellum.

*Aspect.*—Flowers are outward-facing to slightly nodding.

*Vertical height.*—Approximately 11.5 cm.

*Diameter.*—Approximately 11.5 cm.

*Depth.*—Approximately 4.0 cm.

*Fragrance.*—No fragrance.

*Lastingness.*—6 to 8 weeks, on average.

*Persistent.*—Self-cleaning.

*Petals.*—Quantity of Petals — Three unfused petals; two conventional petals and one labellum. Arrangement — One lateral petal on each side. Length — Approximately 5.8 cm. Width — Approximately 5.6 cm. Shape — Reniform to near orbicular. Apex — Obtuse. Base — Cuneate. Margin — Entire; moderately undulated. Pubescence, texture and luster of upper surface — Glabrous, velvety and matte. Pubescence, texture and luster of lower surface — Glabrous, velvety and matte. Color when opening, upper surface — White, near RHS NN155D, and fading to violet towards the apex, near RHS N87B to N87C; petals are heavily dotted purple-violet, near RHS N81C to N81D, and violet, RHS 83A. Color when opening, lower surface — Purple-violet, near RHS N82D and lighter, and fading to violet towards the apex, near N87B; dots from upper surface can be seen from the lower surface; near RHS 83B. Color when fully opened, upper surface — White, near RHS NN155D, and fading to violet, near RHS N87C to N87D, towards the margins and near RHS N87B to N87C towards the apex; petals are heavily dotted violet, near RHS 83A and 83B. Color when fully opened, lower surface — Purple-violet, near RHS N82D and lighter, and fading to violet-blue towards the apex, near 90C; dots from upper surface can be seen from the lower surface; near RHS 83B to 83C. Fading, upper surface — Not fading. Fading, lower surface — Not fading. Venation — Reticulate. Venation color, fully opened, upper surface — White, near RHS NN155D, and fading to violet, near RHS N87C to N87D, towards the margins and near RHS N87B towards the apex. Venation color, fully opened, lower surface — Main vein is purple-violet, near RHS N82B; veins at the margins and apex are violet, near RHS N88A and N88B.

*Labellum.*—Shape — Three-lobed, lateral lobes are ovate and involute; central lobe is oblong and strongly revolute. Length — Central lobe — Approximately 2.2 cm. Lateral lobes — Approximately 1.0 cm. Width — Central lobe — Approximately 1.2 cm. Lateral lobes — Approximately 0.8 cm. Apex, central lobe — Emarginate. Apex, lateral lobes — Obtuse. Base, central and lateral lobes — Cuneate. Margin, central lobe — Irregular; undeeply dentate; slightly undulated. Margin, lateral lobes — Entire; not undulate. Texture and luster of upper surface — Central lobe — Glabrous, velvety, and matte. Lateral lobes — Glabrous, velvety, and matte. Texture and luster of lower surface — Central lobe — Glabrous, velvety, and very slightly glossy. Lateral lobes — Glabrous, velvety, and matte. Color when opening, upper surface — Central lobe — Violet, near RHS 83A; apex is purple, near RHS 79A. Lateral lobes — Purple, near RHS 76D, and dotted violet at the base, near RHS 83B; base tinged yellow-orange, near 17B. Color when opening, lower surface — Central lobe — Violet, near RHS 83A yet darker, and fading to purple-violet towards the base, near RHS 81A. Lateral lobes — Purple, near RHS 76C, and slightly striped violet at the base, near RHS N87C. Color when fully opened, upper surface — Central lobe — Violet, near RHS 83A; apex is purple, near RHS 79A, to greyed-purple, near RHS N186B. Lateral lobes — Purple, near RHS 76D, and dotted violet at the base, near RHS 83B; base tinged yellow-orange, near 17B. Color when fully opened, lower surface — Central lobe — Purple, near RHS 79A, to greyed-purple, near RHS N186B, and fading to purple-violet towards the base, near RHS 81A. Lateral lobes — Purple, near RHS 76C, and slightly striped violet at the base, near RHS N87C. Fading, upper surface — Not fading. Fading, lower surface — Not fading. Venation — No veins visible. Venation color, fully opened, upper surface — Central lobe — No veins visible. Lateral lobes — No veins visible. Venation color, fully opened, lower surface — Central lobe — No veins visible. Lateral lobes — No veins visible.

*Callosities.*—Dimensions — 1.5 cm long and 0.7 cm wide, on average. Color — Purple-violet, near RHS N82C and N82D.

*Spurs.*—Quantity — Average of 1. Length — Approximately 0.7 cm. Diameter — Approximately 0.5 cm. Vertical height — Approximately 0.7 cm, at the base. Shape — Short triangular. Apex — Bluntly acute. Base — Broad Cuneate. Pubescence, texture and luster — Glabrous, smooth, and matte. Color — Purple, near RHS 76C to 76D, and striped darker, near RHS 76B.

*Sepals.*—Quantity — Average of 3 unfused sepals. Arrangement — One dorsal sepal and two lateral sepals. Length — Dorsal sepal — Approximately 5.9 cm. Lateral sepals — Approximately 6.4 cm. Width — Dorsal sepal — Approximately 5.9 cm. Lateral sepals — Approximately 7.0 cm. Shape — Dorsal sepal — Broad ovate to near broad oblong. Lateral sepals — Reniform. Apex, dorsal and lateral sepals — Obtuse. Base, dorsal and lateral sepals — Cuneate. Margin, dorsal and lateral sepals — Entire; all sepals are moderately and coarsely undulated. Pubescence, texture and luster — Glabrous, velvety, and matte on both the upper and lower sepal surfaces. Color when opening, upper surface — Dorsal sepal — White, near RHS NN155D, and fading to violet towards the apex, near RHS N87B to N87C; sepals are heavily dotted purple-violet, near RHS N81C to N81D, and violet, RHS 83A. Lateral sepals — White, near RHS NN155D, and fading to violet towards the apex, near RHS N87B; sepals are heavily dotted violet, near RHS 83A and 83B. Color when opening, lower surface — Dorsal sepal — Purple-violet, near RHS N82B to N82C, and fading to a darker violet towards the apex, near N82A; violet dots from upper surface can be seen from the lower surface; near RHS 83C to 83D. Lateral sepals — Purple-violet, near RHS N82B to N82C, and fading to a darker violet towards the apex, near N82A; violet dots from upper surface can be seen from the lower surface; near RHS 83C to 83D. Color when fully opened, upper surface — Dorsal sepal — White, near RHS NN155D, and fading to violet, near RHS N87C to N87D, towards the margins and near RHS N87B towards the apex; sepals are heavily dotted violet, near RHS 83A and 83B. Lateral sepals — White, near RHS NN155D, and fading to violet, near RHS N87C to N87D, towards the margins and near RHS N87B towards the apex; sepals are heavily dotted purple, near RHS 79A to 79B, and violet, near RHS 83A. Dots on lateral sepals are larger and more densely distributed on the sepals. Color when fully opened, lower surface — Dorsal sepal — Purple-violet, near RHS N82D and lighter, and fading to violet towards the apex, near N82B to N87C; central portion of sepals are tinged purple-violet, near N81C; violet dots from upper surface can be seen from the lower surface; near RHS 86B. Lateral sepals — Purple-violet, near RHS N82D and lighter, and fading to violet towards the apex, near N82B to N87C; central portion of sepals are tinged purple-violet, near N81C; violet dots from upper surface can be seen from the lower surface; near RHS 86B. Fading, upper surface — The color of all sepals dues not fade. Fading, lower surface — The color of all sepals does not fade. Venation — Reticulate. Venation color, fully opened, upper surface — White, near RHS NN155D, and fading to violet, near RHS N87C to N87D, towards the margins and RHS N87B towards the apex; veins near the margins and apex are violet, near RHS 86A. Venation color, fully opened, lower surface — Main vein is purple-violet, near RHS 81C; veins at the margins and apex are violet, near 86A and 86B.

*Pedicels.*—Length — Approximately 6.3 cm. Diameter — Approximately 0.5 cm. Angle — Approximately 60 degree angle to peduncle axis. Strength — Moderate. Texture — Glabrous, axially angled with 5 "ribs", axially twisted (due to resupination). Luster — Glossy. Color — Purple, near RHS N75C and lighter, and slightly darker towards the proximal end, near RHS N75B.

*Bract.*—Quantity — One bract present at the base of each pedicel. Shape — Reniform; folded around the base of each pedicel. Dimensions — Average of 1.7 cm long and 2.0 cm wide. Apex — Broad acute. Base — Broad cuneate. Margins — Entire. Color, both surfaces — Yellow-green, near RHS 150B.

Reproductive organs:

*Column.*—Length — Approximately 0.55 cm. Diameter — Approximately 0.7 cm. Color — White, RHS 155C; upper side is purple, RHS N75B.

*Ovary.*—Position — Inferior. Diameter — Approximately 1.2 cm. Color — Yellow-green, RHS 150D.

*Pollinia color.*—Yellow-orange, RHS 14A.

Seed and fruit: No fruit and seed production has been detected to date.

COMPARISON WITH THE PARENT PLANTS p

Plants of the new cultivar 'SPCDW1507' differ from the unnamed *Vanda* seed parent (not patented) by the characteristics described in Chart 1.

CHART 1

| Characteristic | 'SPCDW1507' | Unnamed seed parent |
|---|---|---|
| Color pattern on the petals and sepals. | Heavily dotted. | Lightly dotted. |
| Flower size. | Smaller flowers than seed parent. | Larger flowers than 'SPCDW1506'. |
| Plant vigor. | More vigorous and faster growing than the pollen parent. | Less vigorous and slower growing than 'SPCDW1507'. |

Plants of the new cultivar 'SPCDW1507' differ from the unnamed *Vanda* pollen parent (not patented) by the characteristics described in Chart 2.

CHART 2

| Characteristic | 'SPCDW1507' | Unnamed pollen parent |
|---|---|---|
| Inflorescence size. | Racemes are longer than those of the pollen parent. | Racemes are shorter than those of 'SPCDW1507'. |
| Color pattern on the petals and sepals. | Heavily dotted. | No pattern is present. |
| Flower size. | Larger flowers than pollen parent. | Smaller flowers than 'SPCDW1507'. |
| Plant vigor. | More vigorous and faster growing than the pollen parent. | Less vigorous and slower growing than 'SPCDW1507'. |

COMPARISON WITH THE MOST SIMILAR *VANDA* CULTIVAR KNOWN TO THE INVENTOR

Plants of the new cultivar 'SPCDW1507' are most similar to the cultivar, *Vanda* 'SPCDW1404' (U.S. Plant Pat. No. 28,325). A comparison of 'SPCDW1507' with *Vanda* 'SPCDW1404' is described in Chart 3.

CHART 3

| Characteristic | 'SPCDW1507' | 'SPCDW1404' |
|---|---|---|
| Leaf attitude. | Less upright than 'SPCDW1404'. | More upright than 'SPCDW1507'. |
| Foliage color. | Darker green compared to 'SPCDW1404'. | Lighter green compared to 'SPCDW1507'. |
| General tonality of the flowers. | Purple-violet. | Violet. |
| Flower size. | Larger flowers than 'SPCDW1404'. | Smaller flowers than 'SPCDW1507'. |
| Undulation of the sepal margins. | More highly undulated. | Less undulation. |

That which is claimed is:

1. A new and distinct variety of *Vanda* plant named 'SPCDW1507', substantially as described and illustrated herein.

* * * * *